(12) United States Patent
Vranicar Savanovic et al.

(10) Patent No.: US 7,553,857 B2
(45) Date of Patent: Jun. 30, 2009

(54) S-OMEPRAZOLE MAGNESIUM

(75) Inventors: Lidija Vranicar Savanovic, Metlika (SI); Dejan Mandic, Ljubljana (SI); Renata Toplak Casar, Logatec (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 11/318,236

(22) Filed: Dec. 23, 2005

(65) Prior Publication Data

US 2007/0149573 A1    Jun. 28, 2007

(51) Int. Cl.
*A61K 31/4439* (2006.01)
*C07D 401/12* (2006.01)

(52) U.S. Cl. .................. 514/338; 546/273.7
(58) Field of Classification Search .............. 546/273.7; 514/338
See application file for complete search history.

(56) References Cited

U.S. PATENT DOCUMENTS

| 6,369,085 | B1 * | 4/2002 | Cotton et al. ................ 514/338 |
| 6,713,495 | B1 * | 3/2004 | Sherman ..................... 514/338 |
| 6,894,066 | B2 * | 5/2005 | Sherman ..................... 514/338 |
| 7,169,793 | B2 * | 1/2007 | Reddy et al. ................ 514/299 |
| 2003/0212274 | A1 * | 11/2003 | Vijayaraghavan et al. ...... 546/2 |
| 2004/0235903 | A1 * | 11/2004 | Khanna et al. .............. 514/338 |

FOREIGN PATENT DOCUMENTS

WO    2006/069159    *    6/2006

OTHER PUBLICATIONS

Chopra et a., "Formulation and, etc.," Pharmacos, 25 (1981), pp. 39-45.*
Caira, "Crystalline Polymorphism, etc.," Topics in Current Chemistry, 198, Springer Verlag Berlin Heidelberg, 1998, 163-208.*
Xu, "Dynamic vapor. etc.," CA 2003:773170, 2003.*
Threifall, "Analysis of Organic Polymorphs A Review" Analyst, 1995, 120, 2435-2460.*
Nerurkar et al., "Properties of Solids, etc.," Transport Processes in Pharmaceutical Systems, NY Marcel Dekker, Inc., 2000, 575-611.*
Hawley's Condensed Chemical Dictionary, 13rh ed., NY: John Wiley & Sons, Inc., 1997, 68.*
Brittain ed., Polymorphism in Pharmaceutical Sciences, NY: Marcel Dekker, 1999, pp. 1-2, 185-226.*
Doelker, enlglish translation of S.T.P. Pharma Pratiques (1999), 9(5), 2999-409, pp. 1-33.*
Muzaffar et al., "Polymorphism and Drug, etc.," J of Pharmacy (Lahore), 1979, 1(1), 59-66.*
Jain et al.,"Polymorphism in Pharmacy", Indian Drugs, 1986, 23(6), 315-329.*
Ulicky et al., Comprehensive Dictionary, etc., NY: Prentice Hall, 1992, 21.*
Singhal et al., Drug Polymorphism, etc., A Advanced Drug Delivery Reviews 56 (2004) 335-347.*
Xu, "Dynamic vapor, etc.," J of Zhejiang University of Technology, 31 (4), 2003, 456-459.*

* cited by examiner

*Primary Examiner*—Patricia L Morris
(74) *Attorney, Agent, or Firm*—Luedeka, Neely & Graham, P.C.

(57) ABSTRACT

The present invention discloses a process for preparing a magnesium salt of S-omeprazole. The S-omeprazole salt preferably has a water content below about 4.8% by weight, a magnesium content of about 3.4-4.0% by weight, calculated on the weight of anhydrous, solvent free S-omeprazole magnesium, and has an optical purity of at least about 85% entantiomeric excess ("e.e."). In addition, the present invention provides a magnesium salt of S-omeprazole which is substantially free of neutral omeprazole, meaning that the product contains less than about 3% by weight of a-sum of neutral S-omeprazole and neutral omeprazole. Moreover, the S-omeprazole magnesium according to the invention preferably has assay of related substances and degradation products of less than about 0.1 % by weight as determined by high performance liquid chromatography (HPLC).

8 Claims, 1 Drawing Sheet

S-OMEPRAZOLE MAGNESIUM

FIELD OF THE INVENTION

The present invention relates in general to the field of pharmaceutical compositions and in particular to the preparation of a magnesium salt of S-omeprazole which may be used in a pharmaceutical composition.

BACKGROUND OF THE INVENTION

S-omeprazole magnesium, the generic name for magnesium bis(5-methoxy-2-[(S)-[(4-methoxy-3,5-dimethyl-2-pyridinyl)methyl]sulfinyl]-1H-benzimidazole), is a well-known gastric proton-pump inhibitor and has been commercially available from AstraZeneca under the brand name NEXIUM since 2001.

The S-enantiomer of omeprazole was prepared by separation of diastereoisomeric mixtures of derivatized omeprazole with further conversion to S-omeprazole isolated as an syrupous substance in WO 92/08716.

A more convenient procedure for preparation of single isomer was done by chiral oxidation of a starting sulphide by cumene peroxide in the presence of titanium catalyst, diethyl tartrate and a base. The process is disclosed in WO 96/02535. The enantioselectivity of the foregoing transformation was high but there was still a need for removing residual (R)-enantiomer and overoxidation products like sulfones.

WO 97/02261 describes a method of further enrichment of S-enantiomer of omeprazole from already partially enriched mixtures by precipitating the racemate in selected solvents.

WO 97/02261 describes enzymatic enantioresolution of omeprazole and an analytical HPLC procedure of enantiomer determination.

WO 03/089408 describes a procedure of removing overoxidation products by extraction of S-enantiomer of omeprazole with water solution having selected pH values.

WO 94/27988 describes a solid form of S-omeprazole magnesium.

WO 95/01977 describes solid omeprazole magnesium with a degree of crystallinity over 70%.

WO 97/41114 describes an improved procedure for preparing omeprazole magnesium and S-omeprazole magnesium with a low content of inorganic impurities.

WO 04/046134 describes an amorphous S-omeprazole magnesium salt in the form of a trihydrate wherein the term trihydrate is used to define a crystalline material in which water molecules are bound in the crystalline lattice.

WO 03/051867 describes separating omeprazole enantiomers by using simulated moving bed chromatography. Separation requires using technologically demanding procedures of chiral column chromatography to provide enantioresolution of 2-pyridinylmethylsulfinyl-1H-benzimidazoles.

Despite the foregoing, there continues to be a need for a process that can be used to prepare S-omeprazole magnesium with high chemical and optical purity on an industrial scale in a technological simple and efficient way.

SUMMARY OF THE INVENTION

In general, the present invention is directed to a process for preparing a magnesium salt of S-omeprazole. The S-omeprazole salt preferably has a water content below about 4.8% by weight, a magnesium content of from about 3.4 to about 4.0% by weight, calculated on the weight of anhydrous, solvent-free S-omeprazole magnesium, and has an optical purity of at least about 85% entantiomeric excess ("e.e."). In addition, the present invention provides a magnesium salt of S-omeprazole which is substantially free of neutral omeprazole, meaning that the product is S-omeprazole magnesium which contains less than about 3% by weight of a sum of neutral S-omeprazole and neutral omeprazole. Moreover, the S-omeprazole magnesium obtained according to the present invention preferably has an assay of related substances and degradation products of less than about 0.1% by weight as determined by high performance liquid chromatography (HPLC).

In one aspect, therefore, the present invention provides an amorphous S-omeprazole magnesium product which is substantially free of neutral omeprazole. A pharmaceutical composition comprising an amorphous S-omeprazole magnesium product, which is substantially free of neutral omeprazole, and at least one pharmaceutically acceptable excipient is also provided. Preferably, the amorphous S-omeprazole magnesium product is further substantially free of neutral S-omeprazole. More preferably, the sum of neutral omeprazole and neutral S-omeprazole in the product is less than about 3% by weight.

In general, the amorphous S-omeprazole magnesium may have an optical purity in the range of from about 85% e.e. to about 99% e.e. Preferably the optical purity is in the range of from about 94% e.e. to about 96% e.e. The chemical purity of the amorphous S-omeprazole magnesium is preferably greater than about 99.90% by weight by HPLC.

In certain embodiments, the amorphous S-omeprazole magnesium may have a water content of less than about 4.8% by weight. The amorphous S-omeprazole magnesium also preferably has a magnesium content in the range of from about 3.4% to about 4.0% by weight.

In another embodiment, the amorphous S-omeprazole magnesium preferably has a specific surface area in the range of from about 0.75 $m^2/g$ to about 12 $m^2/g$.

In another aspect, the present invention provides a substantially chemically pure amorphous omeprazole magnesium having less than about 0.1% by weight of "related substances" and degradation products by HPLC. Preferably the related substances comprise neutral S-omeprazole and of neutral omeprazole. A pharmaceutical composition comprising a chemically pure amorphous omeprazole magnesium, having less than about 0.1% by weight of "related substances" and degradation products, and at least one pharmaceutically acceptable excipient is also provided.

In yet another aspect, the present invention provides a method of treating gastrointestinal inflammatory disease comprising orally administering to a patient in need of such treating a therapeutically effective amount of amorphous S-omeprazole magnesium, which is substantially free of neutral omeprazole, and at least one pharmaceutically acceptable excipient. The present invention also provides a method of treating gastrointestinal inflammatory disease comprising orally administering to a patient in need of such treating a therapeutically effective amount of a substantially chemically pure amorphous omeprazole magnesium, having less than about 0.1% by weight of "related substances" and degradation products by HPLC, and at least one pharmaceutically acceptable excipient.

In still another aspect, the present invention provides a process for the preparation of S-omeprazole magnesium from a racemic omeprazole starting material. The process includes a step of resolving the racemic omeprazole into R-omeprazole and S-omeprazole enantiomers using a chiral column chromatograph having a chiral stationary phase and a mobile phase which is an alcohol in order to elute a fraction of S-omeprazole in the mobile phase. The fraction of S-omeprazole is concentrated in the eluted mobile phase. The S-omeprazole in the eluted mobile phase is reacted with a source of magnesium to form S-omeprazole magnesium. Finally, the S-omeprazole magnesium is precipitated using a substantially nonpolar organic solvent.

In one embodiment of the invention, the chiral stationary phase preferably comprises a coated polysaccharide on a silica support. It is also preferred that the mobile phase alcohol comprise methanol.

In another embodiment of the invention, it is generally preferred that the magnesium source be selected from the group. consisting of magnesium sulphate, magnesium chloride, magnesium 2-ethyl-hexanoate, magnesium citrate, magnesium stearate, magnesium ascorbate, magnesium acetate, magnesium ethanolate, magnesium methanolate, and mixtures of one or more of the foregoing. More preferably the magnesium source comprises magnesium methanolate.

The organic solvent is preferably selected from the group consisting of diethyl ether, methyl t-butyl ether, diisopropyl ether, and mixtures of one or more of the foregoing. More preferably, the organic solvent comprises diethyl ether.

The S-omeprazole and the magnesium source are preferably reacted for a period of time of from about 10 minutes to about 2 hours. The S-omeprazole and the magnesium source are preferably reacted at a temperature of from about 10° C. to about 40° C.

The S-omeprazole magnesium is preferably precipitated at a temperature of from about −30° C. to about 30° C.

DESCRIPTION OF THE INVENTION

Figure 1:
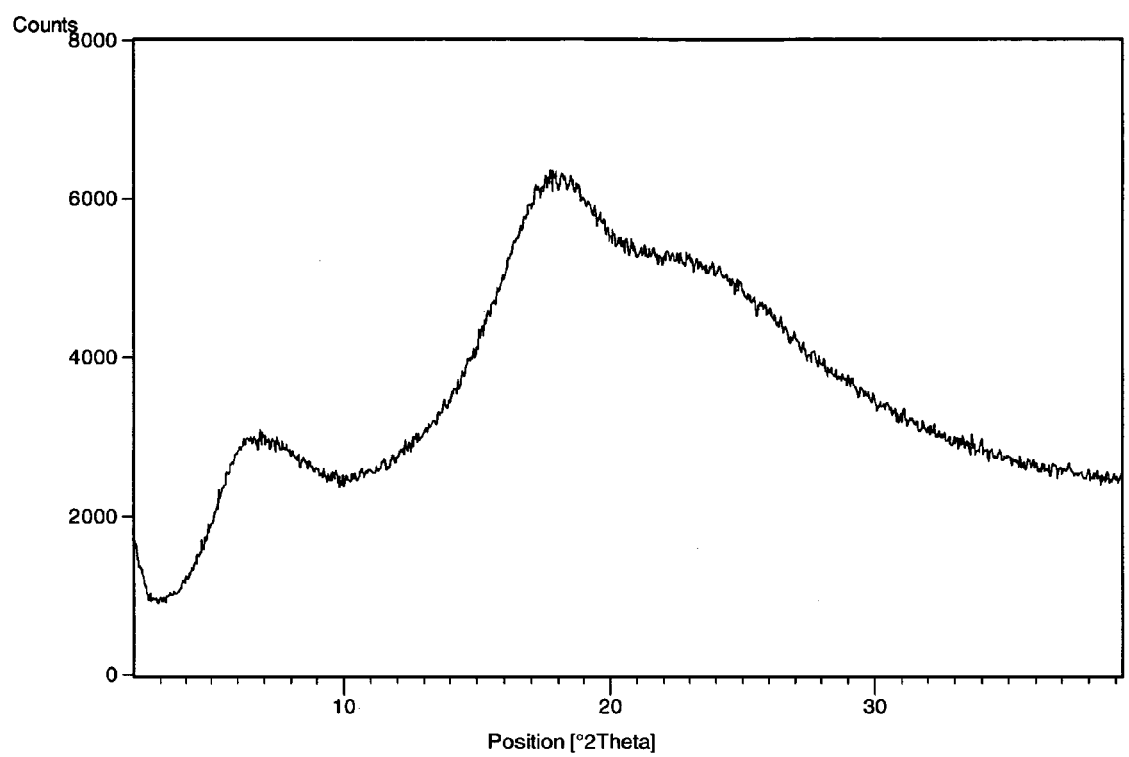
FIG. 1 depicts an X-ray powder diffraction pattern of S-omeprazole magnesium prepared according to one embodiment of the present invention.

The present invention relates to an industrial process for the preparation, purification and isolation of S-omeprazole magnesium having formula (I)

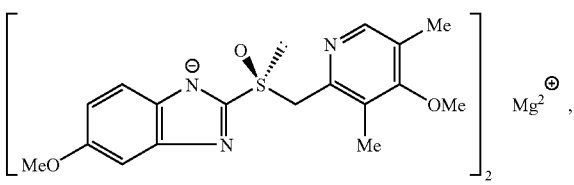

and to an S-omeprazole magnesium salt prepared according to the process of the present invention, having improved characteristics in comparison to the prior art.

In one aspect, the present invention provides a two-step process for the industrial preparation of S-omeprazole magnesium starting from racemic omeprazole. The process comprises at least a separation step carried out by chiral column chromatography to yield S-omeprazole, and a subsequent step of making a magnesium salt of the S-omeprazole by addition of a source of magnesium, such as magnesium methoxide solution, to a concentrated column eluate, and precipitation of the salt in an organic solvent.

In more detail, one embodiment of the industrial process according to the present invention is shown below as Scheme 1. According to Scheme 1, preparation of S-omeprazole magnesium from omeprazole may be accomplished by:

(a) enantioresolution of omeprazole enatiomers by chiral column chromatography using a coated polysaccharide on silica support as a chiral stationary phase and using an alcohol as a mobile phase; and (b) concentration of the column eluates, followed by addition of magnesium methoxide solution as a source of magnesium to the concentrate of S-omeprazole, and final precipitation of S-omeprazole magnesium in an organic solvent and isolation of the separated solid mass by filtration.

Scheme 1

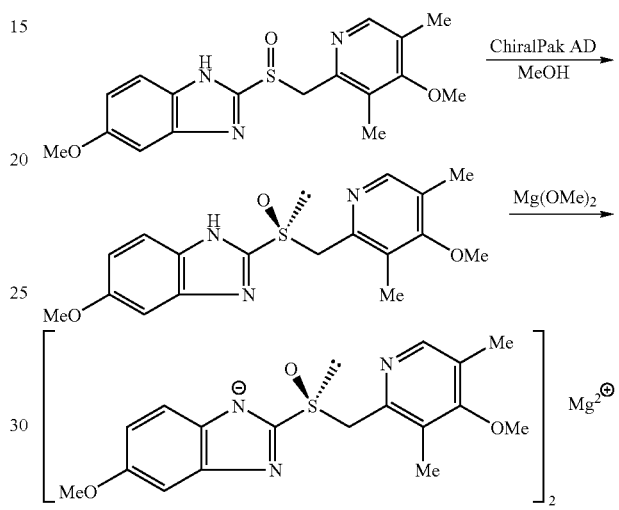

In general, enantioresolution includes the separation of a racemic mixture into its R- and S-enantiomers. Normally, the efficiency of the enantioresolution of any racemic mixture is determined in large part by the selection of an appropriate chiral stationary phase and an appropriate mobile phase. In the present invention, omeprazole may be resolved into its enantiomers using a coated polysaccharide on silica support as the chiral stationary phase. Preferably, the coated polysaccharide is amylose tris(3,5-dimethylphenylcarbamate) and is coated on 20 μm silica gel. This preferred chiral stationary phase, amylose tris(3,5-dimethylphenylcarbamate) coated on 20 μm silica gel, is commercially-available from Chiral Technologies under the trade name CHIRALPAK AD.

An appropriate mobile phase should also be selected which will function properly in conjunction with the chosen chiral stationary phase. If the mobile phase for the chromatographic separation is not carefully selected, the chiral selector, such as amylose tris(3,5-dimethylphenylcarbamate), which actually enables enantioresolution of the racemic mixture, may be mobilized and removed from the stationary phase by the mobile phase. In order to avoid this, producers of chiral stationary phases usually indicate in advance the group of solvents believed to be suitable for use as the mobile phase in conjunction with the chiral stationary phase. For instance, in case of CHIRALPAK AD, the preferred mobile phase is an alcohol, such as methanol or ethanol, in a two component system.

With regard to prior attempts to enantioresolve omeprazole, patent application WO 96/17076 discloses a three component system consisting of methanol/ethanol/hexane for enantioresolution of omeprazole. Additionally, WO 03/051867 teaches against the use of methanol as a mobile phase solvent for separation of enantiomers of omeprazole when using CHIRALPAK AD in simulated moving bed chromatography.

However, it has now surprisingly been found that efficient enantioresolution of omeprazole may be achieved using CHIRALPAK AD as the chiral stationary phase and using a one component mobile phase system which comprises an alcohol such as methanol. Moreover, due to the high efficiency of newly-developed chromatographic system preparative high performance liquid chromatography (PHPLC), it has been found that this process may be used on an industrial scale. Industrial applicability of PHPLC in S-omeprazole preparation is enabled, in part, because CHIRALPAK AD is available in large amounts, thus providing reproducible batch-to-batch properties and at a relatively low cost. The economic feasibility is improved by using a single solvent mobile phase, thus reducing overall solvent costs as compared to more complex multi-component mobile phases. Due to the higher solubility of omeprazole in methanol, a higher loading may be used and consequently a higher efficiency of enantioresolution of omeprazole is achieved. Moreover, enantioresolution using PHPLC method enables fine tuning of expected optical purity of the final product on the basis of sample loading on the column. Thus, S-omeprazole magnesium having an optical purity of at least 85% e.e., preferably at least 89% e.e. may be obtained according to the present invention. In particular, the optical purity of the final S-omeprazole magnesium may range from about 85% e.e. to about 99e.e., and is preferably from about 94% e.e. to about 96% e.e.

Due to the slight acidic environment of alcoholic omeprazole solution it is generally preferred that a small amount of diethylamine be added to the omeprazole solution before loading on the column to improve the stability of the omeprazole in the solution. It has been found that addition of up to about 0.1 V/V%, preferably not more than 0.05 V/V%, is sufficient to ensure efficient stability.

Use of an alcohol mobile phase, such as methanol, has been found to provide several benefits. Advantageously, retention times when using methanol as the mobile phase exhibit a high degree of reproducibility. Consequently, a main fraction of S-omeprazole may be collected during a reproducible time window. This renders the process more easily scalable and ensures a high degree of batch-to-batch uniformity of the final of S-omeprazole product. Thus it has been determined that methanol not only improves dissolution of omeprazole samples loaded on the column into the mobile phase during chromatographic enantioresolution, it also facilitates the design of a very simple and efficient technological process.

Another advantage derived from the methanol-based one component mobile phase of the present invention is that the methanol may be easily recovered from the main fractions by a rectification distillation process and then may be reused in the enantioresolution process. This makes the one component mobile phase system according to the present invention more ecologically friendly.

In a second step of the industrial process of the present invention, the methanolic eluents of S-omeprazole are concentrated and transformed into a magnesium salt by addition of a predefined amount of a magnesium source.

Preferably, the collected eluates of S-omeprazole from the enantioresolution are concentrated to a smaller volume by partial distillation of the mobile phase solvent which is preferably an alcohol such as methanol. A magnesium source is then added to the concentrate of neutral S-omeprazole to produce the S-omeprazole magnesium salt. Suitable magnesium sources for use in the present invention include magnesium inorganic salts such as magnesium sulphate and magnesium chloride; magnesium organic salts selected from a group consisting of magnesium 2-ethyl-hexanoate, magnesium citrate, magnesium stearate, magnesium ascorbate, magnesium acetate, magnesium alcoholate, and mixtures thereof. Preferably, the magnesium source is a magnesium alcoholate, such as magnesium ethanolate or magnesium methanolate. More preferably, magnesium methanolate in a methanol solution is used as magnesium source.

The magnesium source is preferably added in a predefined amount in order to enable control of the magnesium content in the final S-omeprazole magnesium. Magnesium that is added during this stage as magnesium source is consumed to make S-omeprazole magnesium. Thus, if more than one chemical equivalent (corresponding to S-omeprazole in the concentrated solution) of magnesium is added by addition of magnesium source, the remaining magnesium is incorporated in the final product of S-omeprazole magnesium as free surplus magnesium. Conversely, if the magnesium source provides less than one equivalent (regarding S-omeprazole in the concentrated solution) of magnesium, the final S-omeprazole magnesium obtained may also include neutral S-omeprazole and neutral omeprazole as impurities.

Preferably, the magnesium source is added in an amount such that the final product obtained is S-omeprazole magnesium having a magnesium content from about 3.4 to about 4.0% by weight calculated on anhydrous, solvent free S-omeprazole magnesium. Further the final product S-omeprazole magnesium is preferably substantially free of neutral S-omeprazole and substantially free of neutral omeprazole impurities. As used herein, the term "substantially free of neutral S-omeprazole and substantially free of neutral omeprazole" means that the total amount of neutral S-omeprazole and neutral omeprazole impurities included in the product S-omeprazole magnesium obtained according to the present invention is below about 3%, preferably below about 2%, and most preferably below about 1% by weight.

It is desired that product S-omeprazole magnesium be substantially free of neutral S-omeprazole because neutral S-omeprazole exhibits a syrupous or semisolid appearance and associated properties. Thus, further addition of neutral S-omeprazole in the S-omeprazole magnesium may lower the solidity and/or increase the tackiness of the particles, thereby, promoting formation of undesirable agglomerates. These difficulties are limited when the product is substantially free of neutral S-omeprazole and substantially free of neutral omeprazole. Further, as noted above, neutral S-omeprazole and neutral omeprazole are considered as impurities in the S-omeprazole magnesium of the present invention.

The product reaction mixture is preferably stirred at a temperature of from about 10° C. to about 40° C., preferably at about room temperature. The reaction time may range from about 10 minutes to about 2 hours. Preferably the reaction time is from about 20 minutes to about 1.5 hour. Most preferably the reaction time is from about 0.5 to about 1 hour.

After the reaction with the magnesium source is substantially completed, the S-omeprazole magnesium is then precipitated. To the obtained reaction mixture containing S-omeprazole magnesium, a small amount of diatomic filter medium is preferably used to filter off and remove inorganic magnesium salt residues. The filtrate is then poured into a substantially nonpolar organic solvent such as an ether solvent in order to precipitate the S-omeprazole magnesium. Suitable ether solvents for use in the present invention may be selected from the group consisting of diethyl ether, methyl t-butyl ether, diisopropyl ether, and mixtures of one or more thereof. Most preferably, diethyl ether is used for precipitation of S-omeprazole magnesium. The temperature of precipitation medium may be in the range of from about 30° C. to about −30° C., preferably from about 20° C. to about −10° C.

The volume ratio between the reaction mixture containing S-omeprazole magnesium and the nonpolar organic solvent is preferably controlled so as to facilitate the precipitation of the S-omeprazole magnesium. The volume of the reaction mixture containing S-omeprazole magnesium is preferably not greater that about 30% of the volume of the nonpolar organic solvent. The precipitate thus form may be further separated by filtration, washed with a small amount of ether solvent or, optionally, purified by digestion in a small amount of ether solvent. Ether solvents for use in washing or digesting the S-omeprazole magnesium precipitate are preferably selected from the same group as disclosed earlier, i.e., from the group consisting of diethyl ether, methyl t-butyl ether, diisopropyl ether, and mixtures thereof.

The S-omeprazole magnesium product produced according to the present invention has also been found to exhibit improved properties. S-omeprazole magnesium is known to be a highly hygroscopic compound, and it is difficult to remove water from S-omeprazole magnesium. Consequently, it is desirable to produce and maintain S-omeprazole magnesium with as low a water content as possible in order to avoid the need for a difficult dehydration process. Advantageously, the process according to the present invention uses solvents which have a relatively low water content. In particular, the methanol solvent preferably used as a mobile phase for the PHPLC according the present invention can be easily dried using processes known to those of ordinary skill in the art, and in addition, the ether solvents used for the precipitation of S-omeprazole magnesium are generally known as being non-hygroscopic solvents and thus inherently contain very little water. As a result, precipitation of S-omeprazole magnesium in a nonpolar organic solvent enables formation of S-omeprazole magnesium having a water content below about 4.8%, preferably below about 3.2%, and most preferably below about 2.5% by weight.

The preferred use of ether solvents as nonpolar solvents for the precipitation of S-omeprazole magnesium provides the further advantage that the S-omeprazole magnesium precipitate thereby obtained is generally coarse and thus easy filterable. In contrast, use of other nonpolar solvents for the precipitation may lead to the formation of pastelike precipitates which are more difficult to filter.

As noted above, chromatographic enantioresolution of omeprazole using methanol as mobile phase according to the present invention provides for the recovery of S-omeprazole having a relatively low water content from an anhydrous medium. In contrast, when S-omeprazole is prepared by a chemical process the final step of the procedure is generally extraction of the S-omeprazole product from an aqueous medium. In addition, the reaction of S-omeprazole with the magnesium source in accordance with the invention is preferably performed under an inert atmosphere, and the further precipitation of the amorphous solid in ether therefore yields substantially solid S-omeprazole magnesium with a relatively low water content.

The improved characteristics of the S-omeprazole magnesium obtained using the process of the present invention are believed to be due, at least in part, to the use of omeprazole as the starting compound for enantioresolution and a preparative high performance liquid chromatography (PHPLC) process. In terms of impurities, the use of PHPLC enables the substantial elimination of the R-enantiomer of omeprazole as well as substantially all of the impurities associated with chemical synthesis.

The present process for the preparation of S-omeprazole magnesium including enantioresolution provides a very cost effective method of manufacturing a product of high purity on an industrial scale with PHPLC, previously limited primarily to very small-scale uses because of a perception of high cost, complexity, and other drawbacks. The use of PHPLC enables production of high purity S-omeprazole magnesium on an economic basis, contrary to conventional wisdom. The S-omeprazole magnesium obtained as the product of the present invention may have an assay of related substances and degradation products of less than about 0.1% by weight as determined by high performance liquid chromatography (HPLC). In other words, the S-omeprazole magnesium obtained by the process of the present invention may have a purity as high as above 99.9% by weight by HPLC, and may be as high as the starting omeprazole compound itself. This provides a significant and surprising advantage in comparison to known chiral organic synthesis processes, which generally lead to products of substantially lower purity which are not appropriate for direct pharmaceutical applicability. Such synthesis products generally require further purification to provide products suitable for pharmaceutical usage which leads to further loss of product, further changes in the desired polymorphous form of the product, and a further loss of time in production, and higher cost.

The S-omeprazole magnesium prepared according to the present invention is obtained in an amorphous form. FIG. 1 presents an X-ray powder diffractogram of S-omeprazole magnesium obtained by the process disclosed in Example 3 (see below) which shows two broad peaks at positions of around 7 and 18 °2 Theta. The X-ray powder diffractogram was measured on X'Pert PRO MPD a difractometer with CuKα radiation source.

Preferably, the S-omeprazole magnesium obtained by the process of the present invention has a specific surface area of from about 0.75 to about 12 m$^2$/g.

The S-omeprazole magnesium compounds according to the invention may be used for inhibiting gastric acid secretion in mammals and man. In a more general sense, the compounds of the invention may be used for the treatment of gastric acid-related diseases and gastrointestinal inflammatory diseases in mammals and man, such as gastric ulcer, duodenal ulcer, reflux esophagitis and gastritis. Furthermore, the compounds may be used for treatment of other gastrointestinal disorders where gastric antisecretory effect is desirable, e.g., in patients on NSAID therapy, in patients with gastrinomas, and in patients with acute upper gastrointestinal bleeding. They may also be used in patients in intensive care situations, and pre- and post-operatively to prevent acid aspiration and stress ulceration. The compound of the invention may also be used for treatment or prophylaxis of inflammatory conditions in mammals, including man, especially those involving lysozymal enzymes. Conditions that may be specifically mentioned for treatment are rheumatoid arthritis and gout. The compound of the invention may also be useful in the treatment of psoriasis, as well as in the treatment of Helicobacter infections.

For the preparation of pharmaceutical compositions in the form of dosage units for oral administration, omeprazole prepared according to the process of the present invention may be combined with one or more pharmaceutically acceptable excipients including a solid, pulverulent carrier, such as lactose, saccharose, sorbitol, mannitol, starch, amylopectin, cellulose derivatives or gelatin, as well as an antifriction agent such as magnesium stearate, calcium stearate and polyethyleneglycol waxes. The mixture is then pressed into tablets. If coated tablets are desired, the above-prepared core may be coated with a concentrated solution of sugar, which may contain gum arabic, gelatin, talc, titanium dioxide, or with a pharmaceutically acceptable lacquer dissolved in volatile organic solvent or mixture of solvents. To this coating various pharmaceutically acceptable dyes may be added in order to distinguish among tablets with different amounts of active compound present. Soft gelatin capsules may be prepared which contain a mixture of pure omeprazole prepared according to the process of the present invention and vegetable oil. Hard gelatin capsules may contain granules of the active compound in combination with a solid, pulverulent carrier, such as lactose, saccharose, sorbitol, mannitol, potato starch, corn starch, amylopectin, cellulose derivatives, gelatin, and mixtures thereof.

The following examples illustrate the process of the present invention and are not intended to limit the scope of the invention set forth in the claims appended thereto.

EXAMPLES

Example 1

Racemic mixtures of omeprazole were resolved and separated into (S)- and (R)-enantiomers using chiral column chromatography. The omeprazole mixture were dissolved in methanol and diluted to a concentration of about 22-25 g/L. About 0.01 v/v % of diethylamine was also added to the mixtures. The chromatographic separation was carried out under the following conditions:
Stationary phase: CHIRALPAK AD, 20 μm particle size
Column length: 250-350 mm
Mobile phase: methanol
Loading: $m_{LOAD}/S_{COLUMN}$=175-220 mg/cm$^2$, Flow rate=3.8-4.2 cm/min.
Temperature: room temperature
Flow rate during S-enantiomer elution: 5.7-6.2 cm/min.
Flow rate during R-enantiomer elution: 9.0-11.8 cm/min.
UV detector: 325 nm
Run time: 22-26 min.

Combined fractions of S-omeprazole (4 L of a solution containing 16.3 g of S-omeprazole) produced by the chiral column chromatography were then concentrated approximately 100-fold by evaporation to provide a solution containing about 400 g/L of S-omeprazole in MeOH. A 6% solution of Mg(OMe)$_2$ in MeOH was prepared from 0.608 g of magnesium turnings in 45 mL of MeOH along with a catalytic amount of dichloromethane. 45 mL of the prepared solution of Mg(OMe)$_2$ (2.1 g Mg(OMe)$_2$, 0.55 equiv.) was added to the concentrated solution of S-omeprazole. This reaction mixture was stirred for 0.5 hour at room temperature under an inert atmosphere. Then it was slowly poured into 1.6 L of methyl t-butyl ether under vigorous stirring. The suspension was cooled to −10° C. and kept at this temperature for 1 hour to precipitate out the S-omeprazole magnesium product. After filtration and washing with 160 mL of methyl t-butyl ether, the resultant solid was dried at 40° C. under vacuum to obtain 15.6 g of S-omeprazole magnesium having an optical purity of 91% e.e. as determined by chiral HPLC, a 99.92% purity as determined by HPLC, a 4.4% water content as determined by Karl-Fisher titration, a 3.7% Mg content as determined by atomic absorption spectroscopy (MS), and an assay of $C_{34}H_{36}N_6O_6S_2Mg$ (S-omeprazole magnesium) of 100.06% as determined by HPLC).

Example 2

Combined fractions of S-omeprazole (7 L of a solution containing 35.5 g of S-omeprazole) produced by chiral column chromatography under the chromatographic conditions presented in Example 1 were concentrated approximately 100-fold by evaporation to provide a solution containing about 500 g/L of S-omeprazole in MeOH). A 6% solution of Mg(OMe)$_2$ in methanol was prepared from 1.23 g of magnesium turnings in 91 mL of MeOH with a catalytic amount of dichloromethane. 91 mL of the prepared solution of Mg(OMe)$_2$ (4.37 g Mg(OMe)$_2$, 0.50 equiv) was added to the concentrated solution of S-omeprazole. This reaction mixture was stirred for 0.5 hour at room temperature under an inert atmosphere. After filtration through a layer of diatomic filter medium (CELITE), the reaction mixture. was slowly poured into 3.6 L of methyl t-butyl ether at room temperature under vigorous stirring. The suspension was cooled to −10° C. and kept at this temperature for 1 hour to precipitate out the S-omeprazole magnesium product. The product was further filtered and washed with 50 mL of diethyl ether and the solid was dried at 40° C. under vacuum to obtain 35.3 g of S-omeprazole magnesium in amorphous form having an optical purity of 88% e.e. as determined by chiral HPLC, a 99.93% purity as determined by HPLC, a 4.6% water content as determined by Karl-Fisher titration, a 3.5% Mg content as determined by AAS, and an assay of $C_{34}H_{36}N_6O_6S_2Mg$ of 99.6% as determined by HPLC).

Example 3

Combined fractions of S-omeprazole (2130 mL of a solution containing 11.13 g of S-omeprazole) produced by chiral column chromatography under the chromatographic conditions presented in Example 1 were concentrated approximately 100-fold by evaporation to provide a solution containing about 500 g/L of S-omeprazole in MeOH. A 6% solution of Mg(OMe)$_2$ in methanol was prepared from 0.398 g of magnesium turnings in 29 mL of MeOH with a catalytic amount of dichloromethane. 29 mL of the solution of Mg(OMe)$_2$ (1.41 g Mg(OMe)$_2$, 0.50 equiv.) was added to the concentrated solution of S-omeprazole. The reaction mixture was stirred for 0.5 hour at room temperature under an inert atmosphere. Then, the reaction mixture was slowly poured into 0.55 L of diethyl ether at room temperature under vigorous stirring. The suspension was cooled −10° C. and kept at this temperature for 1 hour to precipitate out the S-omeprazole magnesium product. The product was filtered and washed with 50 mL of diethyl ether and the solid was dried at 40° C. under vacuum to obtain 10.8 g of S-omeprazole magnesium in amorphous form having an optical purity of 88% e.e. as determined by chiral HPLC, a 99.91% purity as determined by HPLC, a 4.7% water content as determined by Karl-Fisher titration, a 3.4% Mg content as determined by AAS, and an assay of $C_{34}H_{36}N_6O_6S_2Mg$ of 98.6% as determined by HPLC). An XRD diffractogram of the amorphous S-omeprazole magnesium is shown in FIG. 3.

Example 4

A racemic omeprazole mixture was separated by PHPLC according to the conditions of Example 1 except that the loading amount was 65 g/cm$^2$. Following separation of the racemic mixture, 2.2 L of fractions containing 3.46 g of S-omeprazole were further treated as described in Example 3 to yield 3.15 g of S-omeprazole magnesium in solid amorphous form having an optical purity of >99% e.e. as determined by chiral HPLC, a 99.94% purity as determined by HPLC, a 4.6% water content as determined by Karl-Fisher titration, a 3.4% Mg content as determined by AAS, and an assay of $C_{34}H_{36}N_6O_6S_2Mg$ of 98.9% as determined by HPLC).

While the invention has been described with particular reference to certain embodiments thereof, it will be understood that changes and modifications may be made by those of ordinary skill within the scope and spirit of the following claims:

What is claimed is:

1. A composition comprising at least about 99.9% by weight of amorphous S-omeprazole magnesium having formula (I):

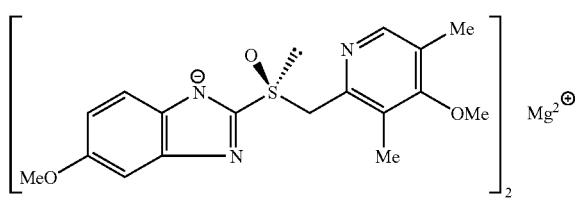

and less than about 0.1% by weight of impurities as determined by HPLC
wherein the amorphous S-omeprazole magnesium has an X-ray powder diffractogram substantially as show in FIG. 1.

2. The composition of claim 1, wherein the impurities comprise neutral S-omeprazole and neutral omeprazole.

3. The composition of claim 1, wherein the amorphous S-omeprazole magnesium has an optical purity in the range of from about 85% e.e. to about 99% e.e.

4. The composition of claim 1, wherein the amorphous S-omeprazole magnesium has an optical purity in the range of from about 94% e.e. to about 96% e.e.

5. The composition of claim 1, wherein the amorphous S-omeprazole magnesium has a water content of less than about 4.8% by weight.

6. The composition of claim 1, wherein the amorphous S-omeprazole magnesium has a specific surface area in the range of from about 0.75 m²/g to about 12 m²/g.

7. The composition of claim 1, wherein the amorphous S-omeprazole magnesium has a magnesium content in the range of from about 3.4% to about 4.0% by weight.

8. A pharmaceutical composition comprising the amorphous S-omeprazole magnesium of claim 1 and one or more pharmaceutically acceptable excipients.

* * * * *